(12) United States Patent
Gooberman

(10) Patent No.: US 8,791,093 B2
(45) Date of Patent: Jul. 29, 2014

(54) PHARMACEUTICAL DELIVERY SYSTEMS FOR TREATMENT OF SUBSTANCE ABUSE AND OTHER ADDICTIONS

(76) Inventor: Lance L. Gooberman, Haddonfield, NJ (US)

( * ) Notice: Subject to any disclaimer, the term of this patent is extended or adjusted under 35 U.S.C. 154(b) by 491 days.

(21) Appl. No.: 12/788,770

(22) Filed: May 27, 2010

(65) Prior Publication Data

US 2010/0311704 A1 Dec. 9, 2010

Related U.S. Application Data

(60) Provisional application No. 61/217,337, filed on May 29, 2009.

(51) Int. Cl.
| | | |
|---|---|---|
| *A01N 45/00* | (2006.01) | |
| *A61K 31/56* | (2006.01) | |
| *A01N 41/12* | (2006.01) | |
| *A61K 31/105* | (2006.01) | |
| *A61K 9/00* | (2006.01) | |
| *A61K 31/145* | (2006.01) | |
| *A61K 31/573* | (2006.01) | |
| *A61K 47/44* | (2006.01) | |

(52) U.S. Cl.
CPC ............ *A61K 9/0019* (2013.01); *A61K 31/145* (2013.01); *A61K 31/573* (2013.01); *A61K 47/44* (2013.01)
USPC .......................................... 514/171; 514/707

(58) Field of Classification Search
None
See application file for complete search history.

(56) References Cited

U.S. PATENT DOCUMENTS

| | | | | |
|---|---|---|---|---|
| 4,678,809 A | * | 7/1987 | Phillips | 514/599 |
| 5,061,729 A | * | 10/1991 | Kincses et al. | 514/562 |
| 5,100,916 A | * | 3/1992 | Johansson et al. | 514/478 |
| 5,407,609 A | | 4/1995 | Tice et al. | |
| 5,486,362 A | | 1/1996 | Kitchell et al. | |
| 5,654,008 A | | 8/1997 | Herbert et al. | |
| 5,792,477 A | | 8/1998 | Rickey et al. | |
| 6,203,813 B1 | * | 3/2001 | Gooberman | 424/422 |
| 6,264,987 B1 | | 7/2001 | Wright et al. | |
| 6,306,425 B1 | | 10/2001 | Tice et al. | |
| 6,358,443 B1 | | 3/2002 | Herbert et al. | |
| 2005/0038062 A1 | * | 2/2005 | Burns et al. | 514/282 |
| 2005/0096304 A1 | | 5/2005 | White et al. | |
| 2005/0245558 A1 | | 11/2005 | Ehrich | |
| 2007/0208134 A1 | * | 9/2007 | Hunter et al. | 525/54.1 |
| 2010/0196436 A1 | | 8/2010 | Gooberman | |
| 2011/0065628 A1 | * | 3/2011 | Johnson et al. | 514/1.1 |

OTHER PUBLICATIONS

Musacchio et al. Inhibition of Dopamine-p-Hydroxylase by Disulfiram In Vivo, The Journal of Pharmacology and Experimental Therapeutics vol. 152, No. 1 1965, p. 56-61.*
Kelly et al. (Am J Obstet Gynecol. Sep. 1993;169(3):568-70).*
McRae, et al., Implications for Internal Medicine, 85(d):779-801 (2001).
Swift, New England J. Med. 340:1482-1490 (1999).
Kick, S., Hospital Practice 34(4):95-106 (1999).
Keung, et al., Proc. Natl. Acad. Sci. USA 95:2198-2203 (1998).
Yourick, et al., Alcohol 4:463-467 (1987).
Yourick, et al., Biochem. Pharmacol. 38:413-421 (1989).
Hart, et al., Alcohol 7:165-169 (1990).
Madan, et al., Drug Metab. Dispos. 23:1153-1162 (1995).
Wilson, Canadian J. Psychiatry 24(6):537-41 (1979).
Gaval-Cruz et al., Molelcular Interventions, 9(4); 175-187 (2000).
Mathias, Nida, 16(1); 2 pages (2001).
Thayer, Chem. Eng. News 84(39:21-44 (2006).
Phillips, M.; Gresser, J.D. Journal of Pharmaceutical Sciences, 1984, v. 73, iss. 12, 1718-1720.
Park, H.; Park, K. Pharmaceutical Research, 1996 v. 13, iss. 12, 1770-1776.

* cited by examiner

*Primary Examiner* — James D Anderson
*Assistant Examiner* — William Lee
(74) *Attorney, Agent, or Firm* — Lerner, David, Littenberg, Krumholz & Mentlik, LLP

(57) ABSTRACT

Disclosed are injectable pharmaceutical compositions that contain a therapeutically effective amount of an anti-addictive agent, an anti-inflammatory agent, and a pharmaceutically acceptable liquid carrier, methods of making the compositions, and uses thereof for treating addictions including substance abuse (or addiction to an abused substance) and addictive or compulsive behavior, by administering the composition to a subject in need thereof.

10 Claims, No Drawings

PHARMACEUTICAL DELIVERY SYSTEMS FOR TREATMENT OF SUBSTANCE ABUSE AND OTHER ADDICTIONS

CROSS-REFERENCE TO RELATED APPLICATIONS

This application claims the benefit of the filing date of U.S. Provisional Patent Application No. 61/217,337 filed May 29, 2009, the disclosure of which is hereby incorporated herein by reference.

BACKGROUND OF THE INVENTION

Substance addiction is a chronic, relapsing disease characterized by a loss of control over drug use, compulsive drug seeking and craving for a substance, use that persists despite negative consequences, and physical and/or psychological dependence on the substance. Substance addiction typically follows a course of tolerance, withdrawal, compulsive drug taking behavior, drug seeking behavior, and relapse. Addictive substances include alcohol, caffeine, nicotine, cannabis (marijuana) and cannabis derivatives, opiates and other morphine-like opioid agonists such as heroin, phencyclidine and phencyclidine-like compounds, sedative ipnotics such as benzodiazepines and barbiturates and psychostimulants such as cocaine, amphetamines and amphetamine-related drugs such as dextroamphetamine and methylamphetamine. Substance abuse and addiction are public health issues. They have significant social and economic impact on both the addict and society by playing a major role in violent crime and the spread of infectious diseases.

According to the World Health Organization, an estimated 13 million people abuse opiates worldwide, including 9 million heroin addicts. More than 25% of opiate abusers die from suicide, homicide, or an infectious disease, such as HIV and hepatitis, within 10-20 years of becoming addicted. Tolerance and physical dependence can develop within two to three days.

The goals for treatment of opiate addiction, as with other types of substance addictions, are to discontinue the use of the opiate while minimizing painful withdrawal symptoms and preventing relapse. Current treatments involve replacing the addictive drug with a substitution of an opioid receptor agonist or mixed agonist/antagonist. An alternative approach consists of the use of an opioid receptor antagonist to block the effect of the agonist.

Alcohol is one of the most commonly abused substances at a global level. Alcoholism leads to serious liver and cardiovascular disease and generates dependence resulting in severe mental disorders, social problems and adverse consequences including the division of families, tragic accidents and the reduction of work performance. According to the WHO, alcohol consumption is responsible for 20-30% of oesophageal and liver cancer, liver cirrhosis, homicides, epilepsy, and motor vehicle accidents world wide. Globally, alcohol abuse leads to about 1.8 million deaths per year. Compulsive behavior towards the consumption of alcohol is a core symptom of the disorder. In recent years several approaches have been investigated to help alcoholic patients to not only control alcohol drinking but also alcohol cravings and relapse.

Several classes of medications such as naltrexone, acamprosate, ondansetron, disulfiram, gamma hydroxybutyrate (GHB), and topiramate have been tested for their potential therapeutic effect on alcohol abuse. Naltrexone, acamprosate, and disulfiram have been proven to be of a certain utility and approved for the treatment of alcoholism. Among these medications, the non-selective opioid antagonist naltrexone is currently considered the pharmacological gold standard.

The National Institute on Drug Abuse estimates that 72 million Americans, about one-third of the population, have tried marijuana. Acute effects of marijuana use include memory and learning problems, distorted perception, difficulty problem solving, loss of coordination, and increased heart rate. Long term abuse can cause the same respiratory problems observed in tobacco smokers, such as daily cough, phlegm production, increased risk of lung infections, and an increased chance of developing cancer of the head, neck and lungs. Depression, anxiety, and job-related problems have been associated with marijuana use. Long term marijuana use can result in addiction with compulsive use that interferes with daily activities. Cravings and withdrawal symptoms, such as irritability, increased aggression, sleeplessness, and anxiety make it difficult for addicts to stop using marijuana.

Psychostimulants, such as cocaine and amphetamines, cause euphoria, increased alertness, and increased physical capacity in humans. These substances first increase dopamine transmission, but long term drug usage results in a reduction of dopamine activity, leading to dysregulation of the brain reward system and dysporia. The WHO estimates 33 million people around the world abuse amphetamines.

Chronic cocaine abuse can result in hyperstimulation, tachycardia, hypertension, mydriasis, muscle twitching, sleeplessness, extreme nervousness, hallucinations, paranoia, aggressive behavior, and depression. Cocaine overdose may lead to tremors, convulsions, delirium, and death resulting from heart arrhythmias and cardiovascular failure. Desipramine, amantadine and bromocriptine have been shown to decrease cocaine withdrawal symptoms.

Amphetamine withdrawal symptoms include EEG changes, fatigue, and mental depression. Tolerance develops over time and may be associated with tachycardia, auditory and visual hallucinations, delusions, anxiety reactions, paranoid psychosis, exhaustion, confusion, memory loss, and prolonged depression with suicidal tendencies. Current treatments for amphetamine addiction include phenothiazines, haloperidol, and chlorpromazine for hallucinations.

BRIEF SUMMARY OF TEE INVENTION

The present invention provides an injectable pharmaceutical delivery system for anti-addictive agents, examples of which include antagonists and aversive agents of substances of abuse, which are useful in the treatment of substance abuse and addictive or compulsive behaviors. Thus, they can be administered non-surgically. In so doing, they provide several advantages compared to subcutaneous implants, such as pellets, or oral dosage forms of anti-addictive agents which require patient compliance. For example, the inventive delivery systems require less time for actual administration and, over the course of time, fewer administrations. Since they are less invasive and do not require surgical incision, there is no need for removal of sutures and there is no scarring. Further, there is less risk of infection. Even further, the presence of the anti-inflammatory agent is believed to decrease any inflammatory response caused by the injection and the presence of a foreign substance, and that attraction of phagocytic cells to the site of injection is reduced.

Accordingly, a first aspect of the present invention is directed to an injectable pharmaceutical composition that contains an anti-addictive agent, an anti-inflammatory agent, and a pharmaceutically acceptable liquid carrier. Methods of making the compositions are also provided. The anti-addictive agent is present in a therapeutically effective amount, which broadly refers to that amount that can result in a reduction, decrease or even a cessation of addictive use or compulsive behavior.

A second aspect of the present invention is directed to a method for treating substance abuse (or addiction to an abused substance) by administering the composition to a subject in need thereof. In certain embodiments, the composition is used to treat a patient with an addition to opioids, psychoactive stimulants, nicotine, and/or alcohol.

A third aspect of the present invention is directed to a method for treating an addictive or compulsive behavior by administering the inventive composition to a subject in need thereof. In certain embodiments, the compulsive behavior is an addiction to gambling, sex or pornography.

DETAILED DESCRIPTION

Pharmaceutical delivery systems of the present invention are useful in the treatment of addiction to substances of abuse, and in the treatment of addictive or compulsive behaviors. The term addiction has been referred to as a recurring compulsion by an individual to engage in some specific activity, despite harmful consequences to the individual's health, mental state or social life. That is to say, it is an uncontrolled, compulsive use or behavior. Embodiments of the present invention may thus be useful in treating addiction to substances of abuse including both recreational drugs and medications alike. Examples of recreational drugs include alcohol, e.g., ethyl alcohol, gamma hydroxybutyrate (GHB), caffeine, nicotine, cannabis (marijuana) and cannabis derivatives, opiates and other morphine-like opioid agonists such as heroin, phencyclidine and phencyclidine-like compounds, sedative ipnotics such as benzodiazepines, methaqualone, mecloqualone, etaqualone and barbiturates and psychoactive stimulants (also known as psychostimulants) such as cocaine, amphetamines and amphetamine-related drugs such as dextroamphetamine and methylamphetamine. Other examples include hallucinogens such as LSD, psilocybin, and ecstasy. Examples of addictive medications include, e.g., benzodiazepines, barbiturates, and pain medications including alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, (e.g., OxyContin™), oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol, tilidine, salts thereof, mixtures of any of the foregoing, mixed μ-agonists/antagonists, and the like.

Examples of addictive or compulsive behaviors that may be treated in accordance with embodiments of the present invention include pathological gambling, sex addiction, addiction to pornography, compulsive overeating, compulsive overexercising, compulsive overexercising, and compulsive use of electronic gadgets and devices such as electronic video games and cellular telephones and communication devices such as BlackBerry® devices.

Anti-addictive agents that may be included in the inventive pharmaceutical delivery systems include antagonists. These agents act upon receptors, typically in the brain (and which may also be present in one or more other organs such as liver, lungs and kidney) and competitively bind the receptor with higher affinity than the agonist, i.e., the substance of abuse. Thus, they effectively block the receptor so as to prevent the body from responding to the substance of abuse, or in the case of compulsive behavior, more generally by blocking the positive reinforcing effect of the behavior. As explained herein, some antagonists useful in the present invention may also produce a weak or partial agonist response. Partial agonists bind and activate a given receptor, but have only partial efficacy at the receptor relative to a full agonist. They may also be considered ligands which display both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone.

In some embodiments, the active agent includes an opioid antagonist. An "opioid antagonist" is an opioid compound or composition including any active metabolite of such compound or composition that in a sufficient amount attenuates (e.g., blocks, inhibits, prevents or competes with) the action of an opioid agonist. These agents exert their activity by acting on one or more opioid receptors. At least three types of opioid receptors, mu, kappa, and delta opioid receptors, have been reported. Opioid antagonists are generally classified by their effects on the opioid receptors. Opioid antagonists may antagonize central receptors, peripheral receptors or both. Naloxone and naltrexone are commonly used opioid antagonist drugs that are competitive in that they bind to the opioid receptors with higher affinity than agonists, but that do not activate the receptors. This effectively blocks the receptor, preventing the body from responding to opiates and endorphins.

Many opioid antagonists are not pure antagonists but also produce some weak opioid partial agonist effects, and can produce analgesic effects when administered in high doses to opioid-naive individuals. Examples of such compounds include nalorphine, and levallorphan. However, the analgesic effects from these drugs are limited and tend to be accompanied by dysphoria, most likely due to action at the kappa opioid receptor. Since they induce opioid withdrawal effects in people who are taking, or have previously used, opioid full agonists, these drugs are considered to be antagonists. Naloxone is one example of an opioid antagonist that has no partial agonist effects. Instead, it is a weak inverse agonist at mu opioid receptors, and is used for treating opioid overdose. Buprenorphine, a semi-synthetic opiate (marketed in the U.S. by Teckitt Benckiser under the tradenames Temgesic, Buprenex, Suboxone and Subutex), is another example of an agent with partial agonist and antagonist actions.

Examples of other opioid antagonists that may be used according to the invention include alvimopan, binaltorphimine, buprenorphine, cyclazocine, cyclorphan, cypridime, dinicotinate, beta-funaltrexamine, levallorphan, methylnaltrexone, nalbuphine, nalide, nalmefene, nalmexone, nalorphine, nalorphine dinicotinate, naloxonazine, naltrendol, naltrindole, oxilorphan, and pentazocine, or their pharmacologically effective esters or salts, or free base forms thereof.

The term "pharmaceutically acceptable salt" refers to a formulation of a compound that does not cause significant irritation to an organism to which it is administered and does not abrogate the biological activity and properties of the compound. Pharmaceutical salts of basic compounds can be obtained by reacting the compound with an acid such as hydrochloric acid, hydrobromic acid, sulfuric acid, nitric acid, phosphoric acid, methanesulfonic acid, ethanesulfonic acid, p-toluenesulfonic acid, salicylic acid and the like. For example, naltrexone hydrochloride is a pharmaceutically acceptable salt of naltrexone. Pharmaceutical salts of acidic compounds can be obtained by reacting the compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts thereof with amino acids such as arginine, lysine, and the like.

In some embodiments, the opioid antagonist is naltrexone. The term "naltrexone" may be used in a general way herein to refer to a free base of naltrexone, a pharmaceutically acceptable naltrexone salt (including hydrates and anhydrous forms, e.g., naltrexone hydrochloride dihydrate and anhydrous naltrexone hydrochloride), a naltrexone metabolite, a naltrexone isomer, a naltrexone prodrug or mixtures thereof. Reference herein to "naltrexone" will be understood as encompassing all such forms, unless the context clearly indicates otherwise.

Opioid antagonists, and particularly naltrexone, may be useful in the treatment of addiction to opioids and opiates (which although refer to natural and synthetic compounds respectively, these terms are commonly used interchangeably, and thus are used herein in a consistent manner). Opioids that may cause such addictive behavior include opioid agonists (natural, semi-synthetic and synthetic alike), partial opioid agonists and mixed opioid agonist/antagonists. Examples of opioids that can be addictive include morphine, codeine, methodone, fentanyl and heroin. Opioid antagonists may also be useful in the treatment of alcohol addiction, nicotine addiction and in the treatment of addictive or compulsive behaviors including pathological gambling, sex addiction, and addiction to pornography, compulsive overeating, compulsive overexercising, compulsive overexercising, and compulsive use of electronic gadgets and devices such as electronic video games and cellular telephones and communication devices such as BlackBerry® devices. While not intending to be bound by theory, it is believed that opioid antagonists such as naltrexone act by blocking the positive reinforcing effect of alcohol or the compulsive behavior, or in the case of alcohol, by blocking the positive reinforcing effect which results from the release of endogenous opioids upon the consumption of alcohol.

The therapeutically effective amount of opioid antagonist contained in the composition may vary, depending upon such factors as the solubility of the opioid antagonist in the carrier, the volume of the composition for injection, and the desired time period over which release of the drug is sought. In general, amounts of opioid antagonist (e.g., naltrexone) effective for treatment ranges from about 200 mg to about 1000 mg, and in some embodiments, about 200 mg to about 500 mg, or about 200 to 300 mg, or about 300 to about 500 mg. Thus, the injectable composition may provide for prolonged release of opioid antagonist (e.g., naltrexone) as to sustain therapeutic blood levels which are typically in the order of about 1 ng/ml blood, for about 2 weeks to about 1 month, 6 weeks, or even about 2 months.

In some embodiments, the anti-addictive agent includes a cannabinoid receptor antagonist. These agents are effective in the treatment of addiction to cannabinoids, nicotine and hallucinogens. The cannabinoid receptors are a class of the G-protein coupled receptor superfamily. Their ligands are known as cannabinoids. There are currently two known subtypes, CB1 which is expressed mainly in the brain, but also in the lungs, liver, and kidney, and CB2, which is mainly expressed in the immune system and in hematopoietic cells. It is also believed that there are novel cannabinoid receptors that is, non-CB1 and non-CB2, which are expressed in endothelial cells and in the CNS. Cannabinoid receptor antagonists may be selective for either the CB1 or CB2 receptor. The present invention contemplates the use of either or both CB1 and CB2 receptor antagonists.

Addictive substances (e.g., alcohol, opiates, Delta(9)-tetrahydrocannabinol (Delta(9)-THC) and psychostimulants, including nicotine), against which the inventive compositions may provide treatment, elicit a variety of chronically relapsing disorders by interacting with endogenous neural pathways in the brain. In particular, they share the common property of activating mesolimbic dopamine brain reward systems, and virtually all abused drugs elevate dopamine levels in the nucleus accumbens. Cannabinoid-1 (CB1) receptors are expressed in this brain reward circuit and modulate the dopamine-releasing effects of Delta(9)-THC and nicotine.

Rimonabant (SR141716), a CB1 receptor antagonist, blocks both the dopamine-releasing and the discriminative and rewarding effects of Delta(9)-THC in animals. Although CB1 receptor blockade is generally ineffective in reducing the self-administration of cocaine in rodents and primates, it reduces the reinstatement of extinguished cocaine-seeking behavior produced by cocaine-associated conditioned stimuli and cocaine priming injections. Similarly, CB1 receptor blockade is effective in reducing nicotine-seeking behavior induced by re-exposure to nicotine-associated stimuli. In human clinical trials, rimonabant was shown to block the subjective effects of Delta(9)-THC in humans and prevents relapse to smoking in ex-smokers. Other examples of cannabinoid receptor CB1 antagonists include rosanabant, taranabant and CP-945598.

Therapeutically effective amounts of these agents that may be present in the injectable compositions generally range from about 100 to about 1000 mg.

In some embodiments, the active agent includes a 5-hydroxytryptamine 3 (5-HT3) receptor antagonist. These agents are known to exert an anti-emetic effect and thus are effective against nausea and vomiting. These agents may be effective in treating addiction to psychoactive stimulants such as cocaine and amphetamines and methamphetamines. Examples of 5-HT3 receptor antagonists that may be useful in the present invention include alosetron, azasetron, bemesetron, cilansetron, dolasetron, granisetron, indisetron, itasetron, ondansetron, palonosetron, propisetron, ramosetron, renzapride, tropisetron, and zatosetron. Therapeutically effective amounts of these agents that may be present in the injectable compositions generally range from about 100 to about 600 mg.

In some embodiments, the anti-addictive agent includes a partial agonist of the nicotinic acetylcholine receptor, and specifically the $\alpha_4\beta_2$ subtype of the receptor. An example is varenicline, marketed in the U.S. by Pfizer under the tradename CHANTIX. Varenicline has been reported to both reduce cravings for and decrease the pleasurable effects of cigarettes and other tobacco products, and through these mechanisms it can assist patients in stopping smoking. Therapeutically effective amounts of these agents that may be present in the injectable compositions generally range from about 100 to about 600 mg.

In some embodiments, the anti-addictive agent includes an aversive agent of a substance of abuse. As used herein, an aversive agent causes unpleasant symptoms in the subject or patient who is consuming the substance of abuse. One such type of agent suitable for use in the present invention is an "alcohol aversive agent", which causes unpleasant symptoms in people who are also consuming alcohol (i.e., ethanol). Thus, inventive pharmaceutical delivery systems that contain an alcohol aversive agent may be useful in the treatment of alcoholism.

The term "alcoholism" includes alcohol abuse and alcohol dependence. The term "alcohol abuse" is defined in the Diagnostic and Statistical Manual of Mental Disorders (DSM-IV). Alcohol abuse as a maladaptive pattern of alcohol use that leads to clinically significant impairment or distress. Symptoms include one or more of the following occurring within a 12-month period: (1) recurrent alcohol use that results in a failure to fulfill major role obligations at work, school or home; (2) recurrent alcohol use in physically hazardous situations; (3) recurrent alcohol-related legal problems; and (4) continued alcohol use despite having persistent or recurrent social or interpersonal problems caused or exacerbated by the effects of the substance. Alcohol dependence may be considered to exist when symptoms of abuse are accompanied by three or more of the following: (1) tolerance defined by either: (a) a need for markedly increased amounts of alcohol to achieve intoxication or desired effect, or (b) markedly diminished effect with continued use of the same amount of alcohol; (2) withdrawal manifested by either: (a) characteristic withdrawal syndrome for alcohol or (b) alcohol taken to relieve or avoid withdrawal symptoms; (3) alcohol taken in larger amounts over a longer period than as intended; (4) a persistent desire or unsuccessful efforts to reduce or control drinking; (5) much time spent in activities necessary to obtain alcohol, use alcohol, or recover from its effects; (6) important social, occupational, or recreational activities being given up or reduced because of drinking; and (7) continued use despite knowledge of having a persistent or recurrent physical or psychological problem caused or exacerbated by alcohol.

Alcohol aversive agents include inhibitors of aldehyde dehydrogenase. ALDH is an enzyme that is involved in the removal of acetaldehyde, a toxic metabolite of alcohol. Although multiple forms of ALDH exist. ALDH-I (also known as ALDH-2) and ALDH-II (also known as ALDH-1) are the major enzymes responsible for the oxidation of acetaldehyde. ALDH-I has a higher affinity for acetaldehyde than ALDH-II, and is thought to be the primary enzyme involved in alcohol detoxification [Keung, W. M., et al., Proc. Natl. Acad. Sci. USA 95:2198-2203 (1998)]. The discovery that 50% of the Asian population carries a mutation in ALDH-I that inactivates the enzyme, together with the low occurrence of alcohol abuse in this population supports the contention that it is this isozyme of ALDH that is primarily responsible for alcohol detoxification. Recent studies also implicate ALDH-I in the metabolism of monoamine neurotransmitters such as serotonin (5-HT) and dopamine (DA) [Keung, W. M., et al., Proc. Natl. Acad. Sci. USA 95:2198-2203 (1998)].

Examples of ALDH inhibitors that may be useful in the present invention include disulfiram, coprine, cyanamide, 1-aminocyclopropanol (ACP), daidzin, cephalosporins, antidiabetic sulfonyl ureas, metronidazole, and any of their metabolites or analogs exhibiting ALDH-inhibiting activity including, e.g., S-methyl N,N-diethyldithiocarbamate, S-methyl N,N-diethyldithiocarbamate sulfoxide, and S-methyl N,N-diethylthiocarbamate sulfoxide.

In preferred embodiments, the injectable composition contains disulfiram. Disulfiram (IUPAC: diethylcarbamothioylsulfanyl diethylaminomethanedithioate, $C_{10}H_{20}N_2S_4$), also known as Cronetal™, Abstenil™, Stopetyl™, Contrain™, Antadix™, Anietanol™, Exhoran™, Antabuse™, Etabuse™, Abstinyl™, Thiuranide™, Esperal™, Tetradine™, Noxal™, Tetraeti™, is a potent irreversible inhibitor of ALDH-II and inhibits ALDH-I only slightly. Recent studies suggest that the inhibition of ALDH-I by disulfiram occurs indirectly via its metabolites, e.g., S-methyl-N,N-diethylthiocarbamate sulfoxide (DETC-MeSO) [Yourick, et al., Alcohol 4:463 (1987); Yourick, et al., Biochem. Pharmacol. 38:413 (1989); Bart, et al., Alcohol 7:165 (1990); Madan, et al., Drug Metab. Dispos. 23:1153-1162 (1995)]. Ingestion of alcohol while taking disulfiram results in the accumulation of aldehydes, which causes tachycardia, flushing, diaphoresis, dyspnea, nausea and vomiting (also known collectively as the disulfiram or disulfiram-ethanol reaction). More simply, this drug produces sensitivity to alcohol which results in a highly unpleasant reaction when the patient under treatment ingests even small amounts of alcohol. In addition to treatment of alcoholism, pharmaceutical delivery systems of the present invention that include disulfiram may also be useful in treatment of addiction to psychoactive stimulants, particularly addiction to cocaine.

The amount of the aversive agent such as disulfiram contained in the composition may vary depending upon such factors as the potency of the agent, the volume of the injection and the desired time period over which release of the drug is sought. In general, amounts of the aversive agent (e.g., disulfiram) effective for treatment (e.g., of alcoholism or addiction to psychostimulants such as cocaine) ranges from about 350 mg to about 1200 mg, and in some embodiments, about 500 mg to about 800 mg.

Combinations (e.g., mixtures) of two or more anti-additive agents, useful for the same purpose, may be present in the composition.

Anti-inflammatory agents present in the inventive compositions are effective to reduce blood flow to cellular elements, whether steroidal or non-steroidal, i.e., non-steroidal anti-inflammatory delivery (NSAID, e.g., salicyclate, ketorolac, naproxen, ibuprofen). Without intending to be bound by any particular theory of operation, Applicant believes that the presence of the anti-inflammatory agent decreases the inflammatory response caused by the injection and the presence of a foreign substance, and that attraction of phagocytic cells to the site of injection is reduced. Applicant also believes that the hydrophobicity of steroidal anti-inflammatory agent keeps water away from the anti-addictive agent such as naltrexone, thus, maximizing amount of injected drug available for sustained absorption.

By way of example, some steroids useful herein include betamethasone dipropionate, betamethasone phosphate, betamethasone valerate, clobetasol propionate, cortisone acetate, dexamethasone phosphate acetate, dexamethasone micronized, fluocinonide, hydrocortisone acetate, hydrocortisone sulfate, methyl prednisone acetate and triamcinolone acetonide.

The amount of anti-inflammatory compound may vary depending upon factors as the amount of drug to be released in a desired time, and the volume of the composition administered. In general, the amounts range from about 10 mg to about 120 mg, and in some embodiments from about 20 mg to about 80 mg, and in yet other embodiments, from about 30 mg to about 60 mg.

The pharmaceutically acceptable carrier (or vehicle) includes a biodegradable or bioerodible liquid. Both non-aqueous and aqueous liquids alike may be useful. The agents may be soluble in the carrier (in which case it may be referred to as a solvent), thus forming an injection solution, or insoluble in which case the injectable composition is in the form of a suspension or dispersion (in which case the carrier may be referred to as a suspension or dispersion medium).

Examples of non-aqueous carriers include edible oils typically vegetable oils. Examples of edible oils that may be useful in the present invention include cottonseed oil, corn oil, almond oil, ground nut corn oil, germ olive oil, germ olive oil, castor oil, and sesame oil. Derivatives of the oils, such as hydrogenated forms of these oils, may also be useful. In some embodiments, cottonseed oil, almond oil, sesame oil, or a corn oil is present. Peanut and olive oils are less preferred. In the case of aqueous suspensions, the compositions may also contain, in addition to water, a dispersing or suspending agent, examples of which include synthetic and natural gums such as tragacanth, acacia, alginate, dextran, cellulose derivatives, (e.g., sodium carboxymethylcellulose and methylcellulose), polyvinyl-pyrrolidone, and gelatin.

The volume of carrier generally ranges from about 2 to about 10 ml, and in some embodiments, from about 2 to about 5 ml, and in yet other embodiments, from about 3 to about 4 ml.

The composition is fluid to the extent that easy syringability exists. It also should be stable under the conditions of manufacture and storage and be preserved against the contaminating action of microorganisms such as bacteria and fungi. Thus, a preservative may be present. Exemplary preservatives include materials that inhibit bacterial growth, such as hydroxybenzoates (e.g., ethyl and propyl hydroxybenzoates such as Nipagen™ and Nipasol™), alcohol (e.g., lower alkanols such as ethanol), antimicrobial agents, benzoic acid, sodium benzoate, benzyl alcohols, sorbic acid, parabens, isopropyl alcohol and others known to one of ordinary skill in the art. Proper fluidity can be maintained, for example, by the use of a coating such as lecithin, by the maintenance of the required particle size in the case of dispersion, and by the use of surfactants. Isotonic agents such as sugars, sodium chloride, or polyalcohols such as mannitol and sorbitol, may also be present in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by sterilization (which can be conducted in accordance with standard pharmaceutical techniques, such as radiation, heat and filter sterilization). Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

The injectable compositions of the present invention are typically administered subcutaneously (e.g., in the abdomen) or intramuscularly (e.g., gluteally, or in the arm or leg). The timing of the injection will vary on several factors, including the overall health of the subject (a human or laboratory animal), the severity of the addiction being treated, and the like. In the case of opioid addiction, administration should be given after withdrawal symptoms have substantially subsided (which are often ameliorated as a result of a detoxification procedure). In the case of alcohol abuse, the patient should not have alcohol in the system; otherwise, administration of the inventive composition (e.g., containing disulfiram) will cause a severely unpleasant reaction. A breath test can be administered beforehand. In general, duration of treatment using the inventive compositions is within the discretion of the medical clinician. Typically, treatment continues so as to achieve 1-2 years of abstinence and participation in a recovery program such as a version of the 12-step program.

The invention will now be described in accordance with the following non-limiting working examples.

Example 1

Inventive Formulation

| Ingredient Listing | Qty. | Unit |
|---|---|---|
| Naltrexone | 2.000 | g |
| Triamcinolone Acetonide (micronized), USP | 0.200 | g |
| Benzyl Alcohol, NF | 2.0 | mL |
| Cottonseed Oil, NF | 5.0 | mL |
| Cottonseed Oil, NF | q.s. to 10.0 | mL |

The formulation described above was prepared to prepare a 10 ml composition containing Naltrexone 200 mg/mL, Triamcinolone Acetonide 20 mg/mL. The composition was prepared by the following steps, namely: sterilize and depyrogenate all heat stable, reusable materials and equipment, then returned to ambient temperature; triturate the naltrexone to form a fine, homogeneous powder; combine and mix the powder and the micronized triamcinolone acetonide, thus forming a homogeneous powder blend; prepare a liquid preparation by combining and mixing the benzyl alcohol and the cottonseed oil (in an amount of 5.0 mL plus processing error adjustments, e.g., typically in the order of less than 5%), thus preparing a homogeneous liquid-like solution; incrementally adding the homogeneous powder blend to the homogeneous liquid-like solution, with continuous mixing, thus preparing a homogeneous liquid-like dispersion; add the additional cottonseed oil to the mixture to fill the required batch size of 10.0 mL plus processing error adjustments, with continuous mixing, thus forming a homogeneous liquid-like dispersion; transfer the final product into the recommended dispensing container, and a smaller quantity into a separate dispensing container, which is to be used as the test sample for sterility and endotoxin testing; pursuant to manufacturer's specifications, dry-heat sterilize the mixture, then return to ambient temperature and pressure, wherein the heating is conducted at about 160° C., and the heating time is conducted for 60 minutes. The temperature of the heated chamber must reach about 121° C. before exposure duration is timed. The test sample is validated for sterility and endotoxins in accordance to current U.S.P. 797 Regulatory Guidelines.

Example 2

Three (3) mls of the formulation of example 1 were injected into patients for purposes of treatment of opiate addiction. The table below shows levels of naltrexone in saliva (in ng/ml) after various time periods post-injection. Patients 2 and 3 were administered two injections at different time periods. All other patients were administered one injection.

| Patient Number | Days After Injection | Naltrexone Level ng/ml |
|---|---|---|
| 1 | 3 | 3.7 |
| 1 | 12 | 7.8 |
| 1 | 28 | 46.9 |
| 2 (first injection) | 2 | 8.8 |
| 2 | 7 | 1.5 |
| 2 | 28 | 0.6 |
| 2 (second injection administered after first sample) | 28 (after second injection) | 22.0 |
| 3 | 0 | 325.5 |
| 3 | 36 (based on sample taken before second injection) | 1.4 |
| 3 (second injection administered after first sample) | 0 (based on sample taken after second injection) | 140.9 |
| 3 | 36 (after second injection) | 0.6 |
| 4 | 0 | 11.8 |
| 4 | 31 | 42.4 |
| 5 | 3 | 4.7 |
| 6 | 60 | 5.0 |
| 7 | 34 | 0 |

Example 3

Inventive Formulation #2

| Ingredient Listing | Qty. | Unit |
|---|---|---|
| Triamcinolone Acetonide (micronized), USP | 1.500 | g |
| Carboxymethylcellulose Sodium, USP | 0.23 | g |
| Sodium Chloride, USP | 0.25 | g |
| Benzyl Alcohol, NF | 0.3 | mL |
| Polysorbate 80 1.2% Solution † | 1.0 | mL |
| Sterile Water for Injection, USP | q.s. to 30.0 | mL |

† Polysorbate 80 1.2% Solution
Polysorbate 80, NF 0.6 mL
Sterile Water for Injection, USP 50.0 mL The inventive formulation above was prepared according to the following protocol, namely: following the manufacturer's specification, sterilize and depyrogenate all heat stable, reusable materials and equipment, then return to ambient temperature; incrementally add the Polysorbate 80 (0.6 mL) to the sterile water for injection (50.0 mL), with continuous mixing until homogeneously dispersed, thus forming a homogeneous liquid-like solution; combine and mix micronized triamcinolone acetonide, carboxymethylcellulose sodium, and sodium chloride to form a homogeneous powder blend; combine and mix the homogeneous liquid-like solution of the Polysorbate 80 with benzyl alcohol, thus producing a homogeneous liquid-like solution; add that solution to the homogeneous powder blend with gentle mixing, thus forming a homogeneous liquid-like dispersion; add sterile water to the mixture to fill to the required batch size (30.0 mL plus processing error adjustments), with continuous mixing, thus forming a homogeneous liquid-like dispersion; transfer the final product into the recommended dispensing container, preferably with continuous mixing during the transfer process in order to maintain homogeneity; following the manufacturer's specifications, autoclave sterilize the mixture (at a heating temperature of 121° C. for 30 minutes, beginning as of the time the heated chamber reaches 121° C.), then return to ambient temperature and pressure (15 psi); and validate the test sample for sterility and endotoxins, in accordance to current P.S.P. 797 Regulatory Guidelines.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An injectable composition comprising a therapeutically effective amount of one anti-addictive agent which is disulfiram, a steroidal anti-inflammatory agent, and a pharmaceutically acceptable liquid carrier comprising a vegetable oil.

2. The composition of claim 1, wherein the steroidal anti-inflammatory agent is triamcinolone acetonide.

3. The composition of claim 1, wherein the liquid carrier further comprises water.

4. The composition of claim 3, further comprising a dispersing agent.

5. The composition of claim 1, wherein the vegetable oil is selected from the group consisting of cottonseed oil, almond oil, corn oil and sesame oil.

6. The composition of claim 1, further comprising a preservative.

7. The composition of claim 6, wherein the preservative is benzyl alcohol, benzyl benzoate, or a mixture thereof.

8. A method for treating alcoholism or cocaine addiction, comprising administering, via injection, a composition comprising one anti-addictive agent which is disulfiram, a steroidal anti-inflammatory agent, and a pharmaceutically acceptable liquid carrier which comprises a vegetable oil, to a human subject in need thereof.

9. The method of claim 8 for treating alcoholism.

10. The method of claim 8 for treating cocaine addiction.

* * * * *